Figure 1:
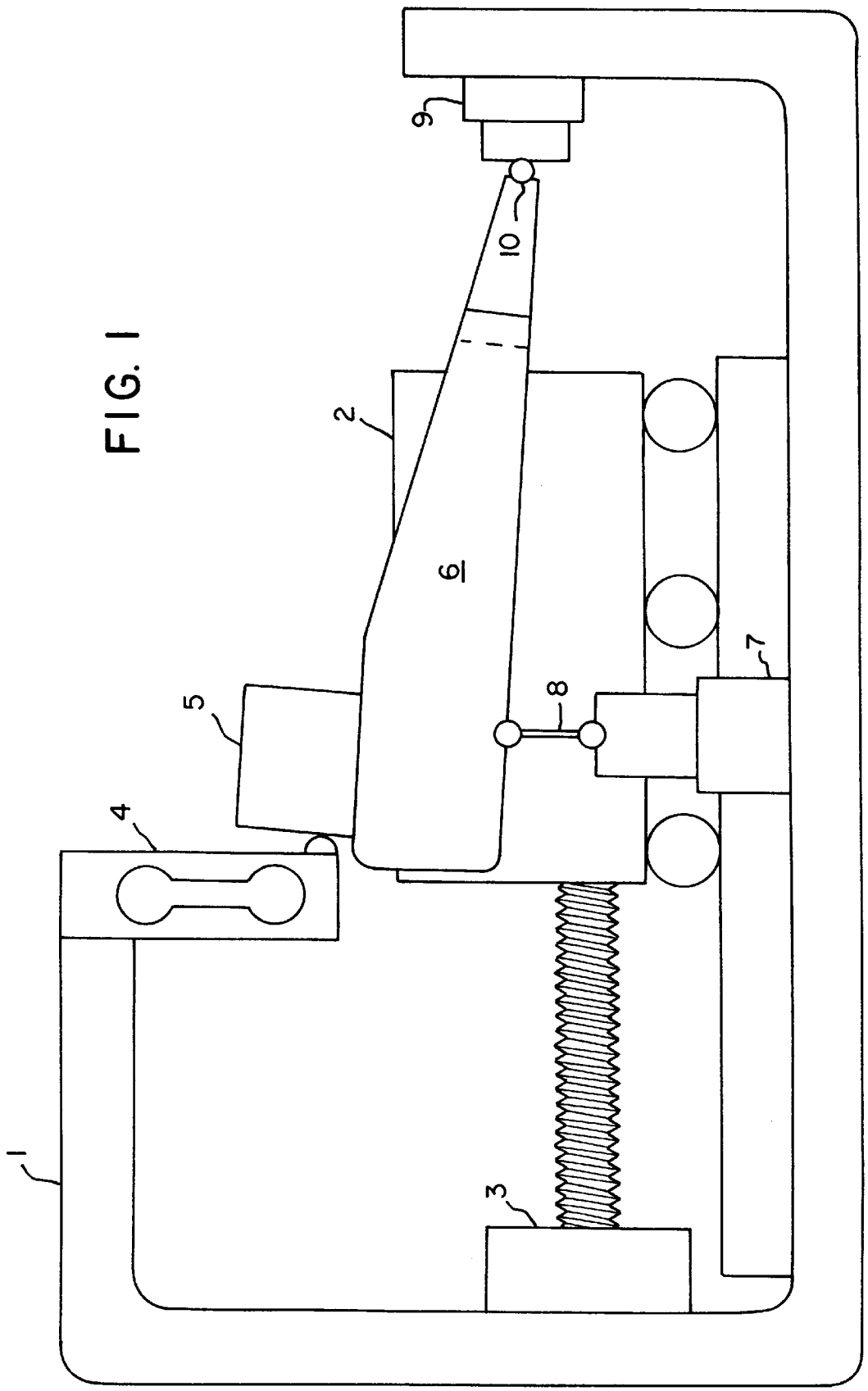
Figure 2:
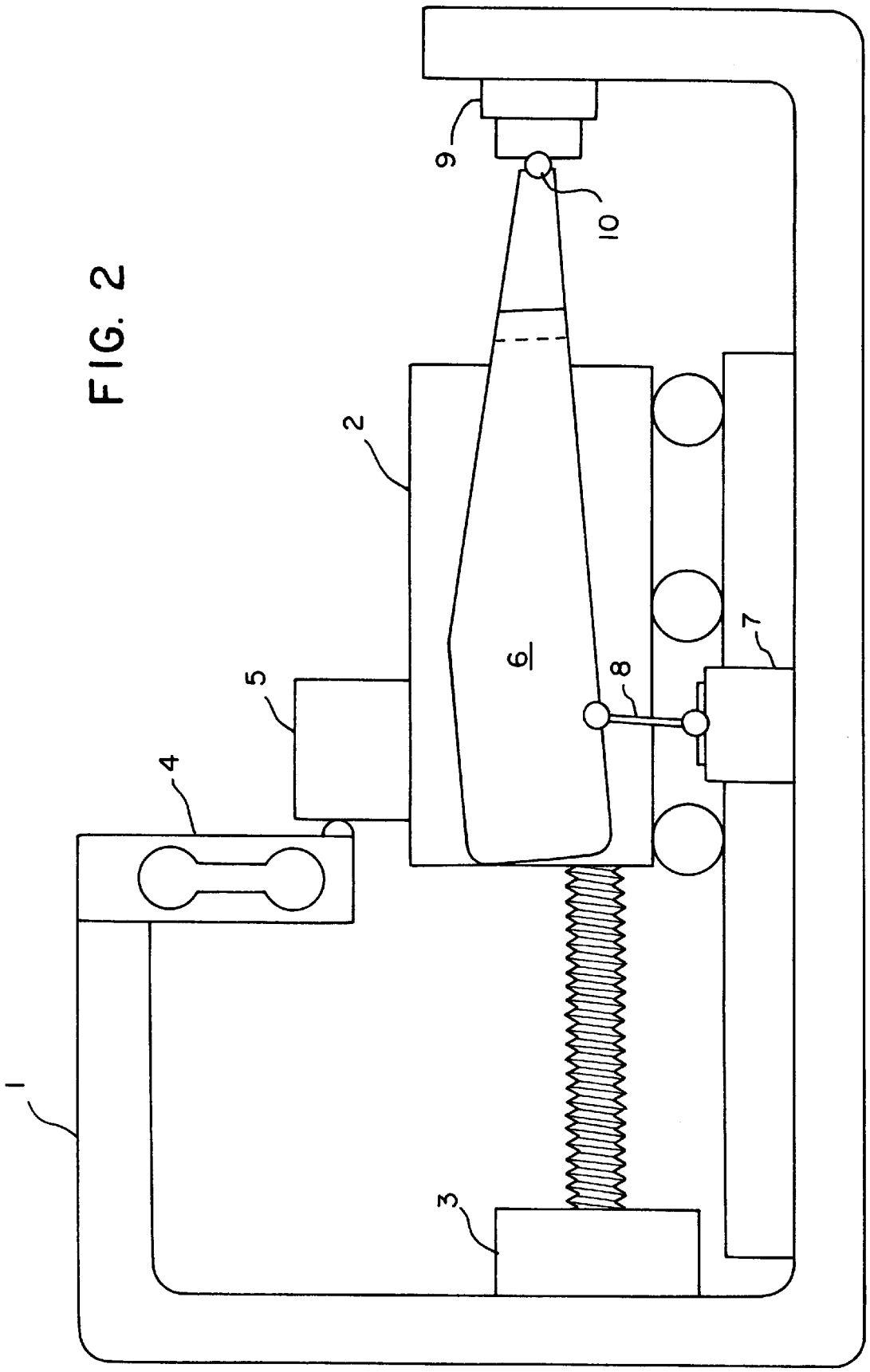
Figure 3:
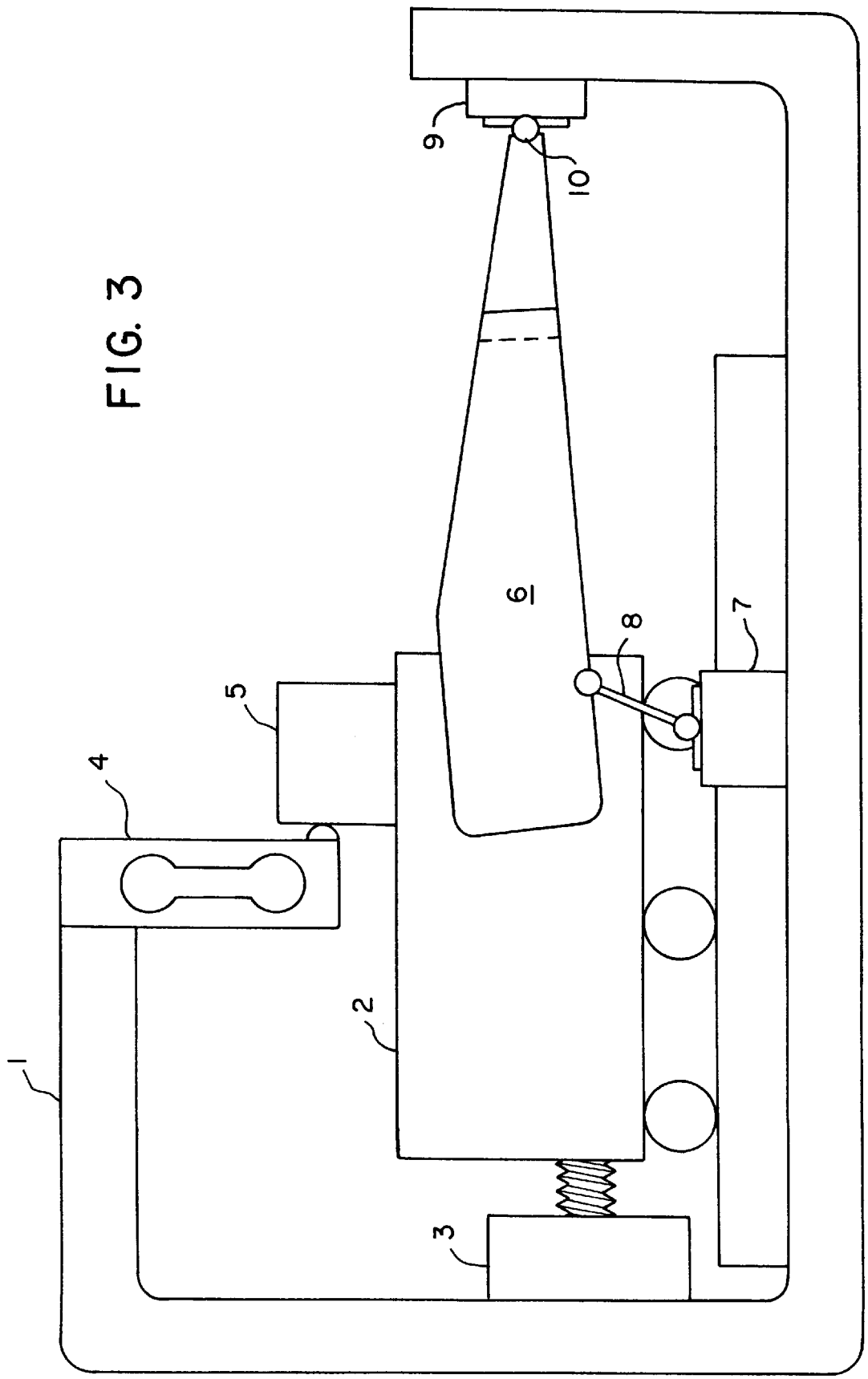
Figure 4:
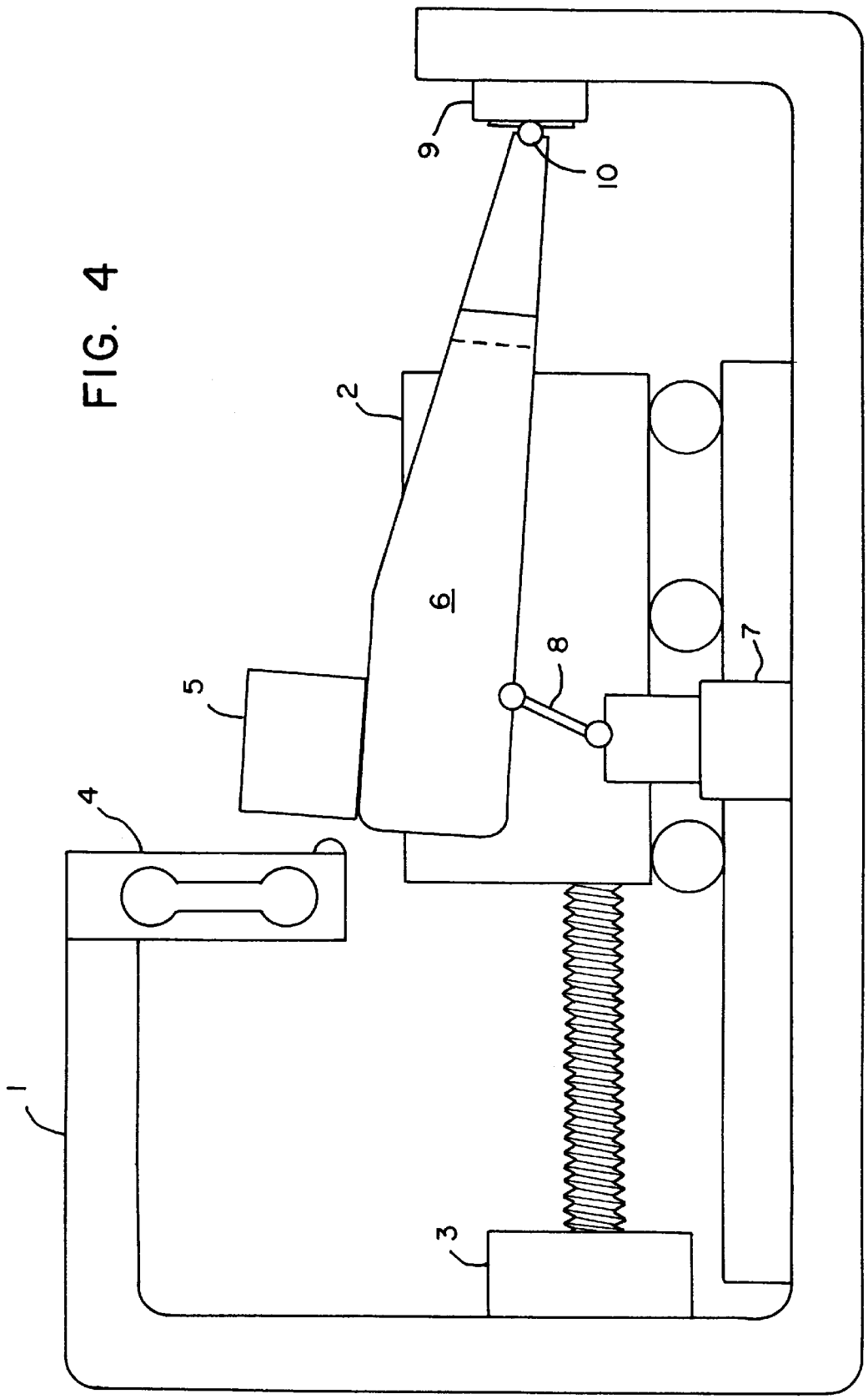
Figure 5:
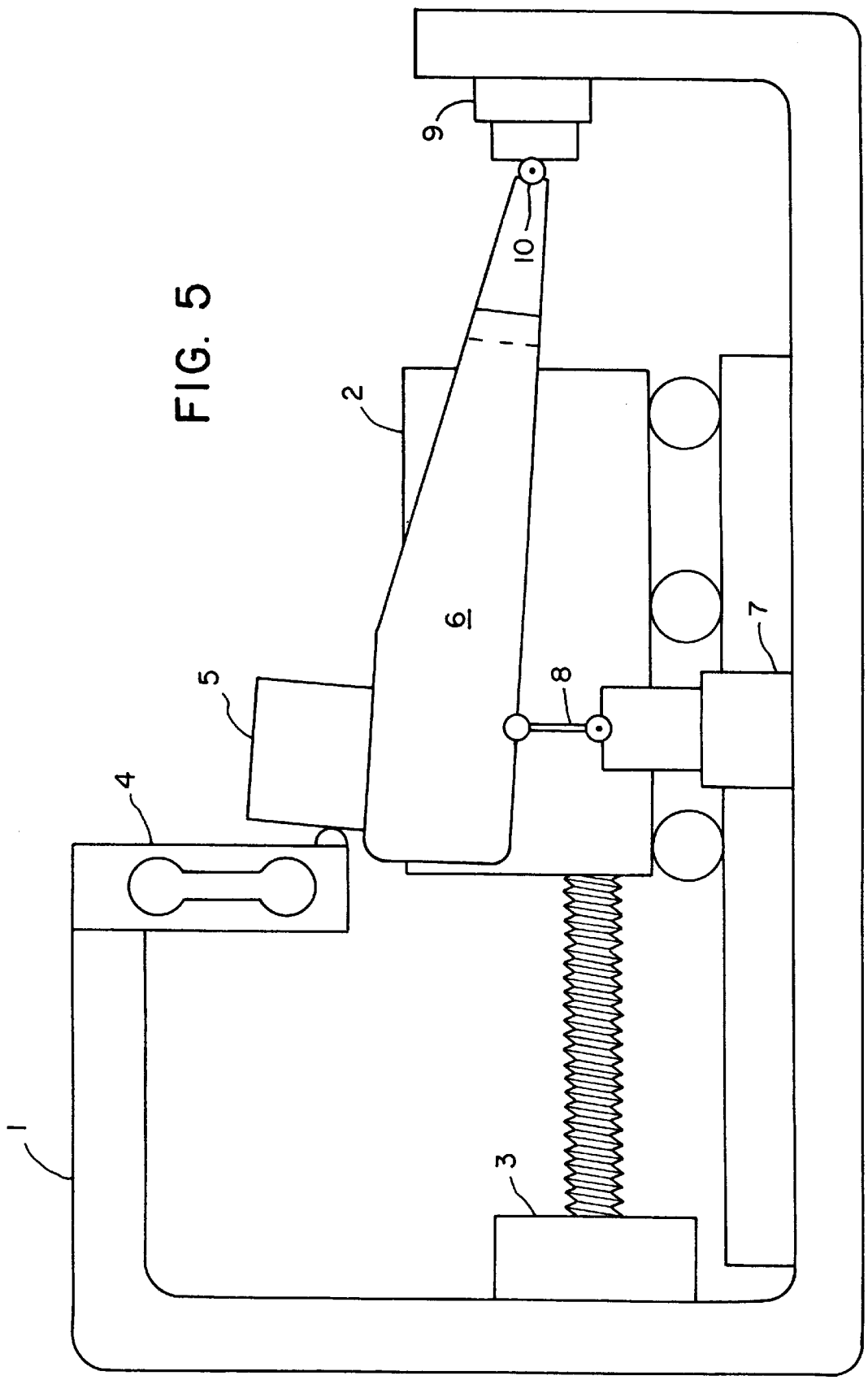

United States Patent [19]
Gunderson

[11] Patent Number: 5,907,090
[45] Date of Patent: May 25, 1999

[54] APPARATUS FOR MEASURING STATIC AND KINETIC FRICTION PROPERTIES

[76] Inventor: Dennis E. Gunderson, 602 Sheldon St., Madison, Wis. 53711

[21] Appl. No.: 09/072,817

[22] Filed: May 6, 1998

[51] Int. Cl.⁶ .................................................. G01N 19/02
[52] U.S. Cl. ........................................................ 73/9
[58] Field of Search .................................... 73/9; 414/258, 414/259, 260

[56] References Cited

U.S. PATENT DOCUMENTS

| | | | |
|---|---|---|---|
| 4,594,878 | 6/1986 | Abe et al. | 73/9 |
| 4,712,418 | 12/1987 | Augustin | 73/9 |
| 5,377,526 | 1/1995 | Diekmann et al. | 73/9 |

Primary Examiner—Hezron Williams
Assistant Examiner—Thuy Vinh Tran
Attorney, Agent, or Firm—William J Connors

[57] ABSTRACT

The disclosure describes an apparatus for measuring the static and kinetic friction properties of sheet materials. The apparatus comprises a sled, moving table, means for creating and measuring the friction force between sled and table, and lift mechanism which places sled on table, and removes sled from the table. Novel aspects include a lift design which causes the sled to be maintained in positive contact with the force measuring means, friction force creating means which integrate a small displacement static forcing means with a mechanically stiff kinetic drive, and sled construction which securely clamps a flat test-piece on a flat plate.

19 Claims, 8 Drawing Sheets

APPARATUS FOR MEASURING STATIC AND KINETIC FRICTION PROPERTIES

BACKGROUND

The measurement of friction force between two flat surfaces is routinely performed using an object of known weight having a flat bottom surface (a "sled"), and a larger, flat, horizontal surface (the "table"). The sled rests on the table with the friction surfaces to be evaluated in contact. A shear force is applied which tends to cause sled and table to slide with respect to one another. The force required to initiate sliding is called the static friction force, the force required to sustain sliding, the kinetic friction force.

While elementary in concept, the actual test is often problematic. It is not uncommon to find that when friction force is evaluated by different test technicians, or on different instruments, significantly different results are obtained. Recent research has shown that friction force can be changed by what appear to be minor differences in the way in which the test is performed, and by inadvertent contamination of the test-pieces by the operator. These findings place stringent new demands on test standards, procedures and instruments to control relevant variables and to prevent the operator from influencing the test results.

DESCRIPTION OF THE INVENTION

The present invention teaches three novel means to control critical elements of the friction test for sheet materials.
Lifting and Placing the Sled The first of these novel means relates to how contact is established between the surfaces to be tested; and more specifically to the placement of the sled on the table, lifting of the sled at the end of a kinetic friction stroke, and positioning of the sled prior to initiation of additional strokes. The novel "lift-and-place" means, which is the subject of this invention, is depicted schematically in FIGS. (1–5) at five different "stages" of a test in which there are to be repeated friction "strokes" of the same test specimen.

Whether on the first stroke or subsequent "repeat" strokes, it is essential that the sled be placed on the table in a precisely controlled way prior to each stroke. In addition to being placed "squarely" on the table, the sled must maintain contact with the force measurement means both as the sled is being placed in contact with table, and as it rests on the table after having been placed there by the lift-and-place means. This requirement can be difficult to meet when considering only the first pass of a friction test,—and is a greater challenge when a series of repeat strokes are to be made. When a series of repeat strokes are to be made, the sled must be lifted out of contact with the table at the end of the "forward" stroke of the table, i.e. before the table is returned to its "starting" position. As the sled is lifted from the table, contact between sled and the force measurement means is likely to be lost, and must be re-established prior to initiation of the next test stroke. The present invention teaches novel and effective means to accomplish this. It is depicted in FIGS. (1) through (5).

FIG. (1) depicts the "lift-and-place means" in relationship to the components of an elementary friction test apparatus. The elementary friction apparatus comprises: a stationary frame (1), a table (2) mounted so as to permit linear translation relative to said frame, drive means (3) capable of causing said table to translate in a horizontal direction along the frame, force measurement means (4) fixedly mounted to frame (1), and sled (5) which is not attached or connected to any other element, but to which specimens of a test material may be affixed.

The lift-and-place means comprises: a forked lift-arm (6), positioned such that one tine is located on each side of the table, a vertical actuator (7) fixedly mounted to the frame and connected to lift-arm (6) by vertical link (8), a horizontal actuator (9) fixedly mounted to the frame and connected to lift-arm (6) at its shank end by ball-connector (10). (Only one tine of the lift-arm is visible in FIGS. 1–5.) Link (8) is connected to the vertical actuator (7) and to the lift-arm (6) by ball-connectors (well known in the art). The ball-connector allows angular misalignment between components without introducing a torque or moment. When used at both ends of a link, the link transmits only linear force along its axis.

A ball-connector (10) is also used to connect horizontal actuator (9) to the shank-end of the forked lift-arm (6). Configured thus, the lift-arm can be moved in a generally fore-aft direction by actuator (9), and the forked end of the lift-arm can be raised and lowered by actuator (7). The sled is of such size as to rest across (be supported by) the two tines of the fork which span the width of the table.

The sequence of movements which causes contact to be maintained between the sled and force measurement means while placing the sled on the table is described in the following paragraphs.

In FIG. (1) the lift-arm is shown in its "up-forward" position, i.e. held "up" by the vertical actuator (7), and "forward" by the horizontal actuator (9). Envision that the operator conducting the test has manually placed the sled (5) on the lift-arm (6) and then pushed the sled forward on the lift-arm (to the left in FIG. 1) until it has come in contact with the force measurement means (4). The sled is not in contact with the table (2), but is supported entirely by the lift-arms. The sled can, therefore, be moved fore and aft on the lift-arms, by force sufficient to overcome the friction force at the contact between the load-arms and the sled. The friction surfaces to be evaluated (on sled and table) are not in contact at this time, and are, therefore, not effected by movement of the sled on the lift-arms.

Prior to start of the friction test, the lift-arm (6) must be lowered, to place the sled (5) into contact with the surface of the table (2),—and then further lowered to move the lift-arm free of contact with the sled. FIG. (2) shows the lift-arm in its "down-forward" position. As the lift-arm moves from the up-forward to down-forward positions the lift-arm not only lowers the sled, but also tends to move the sled forward (to the left in the figure) into contact with the force measurement means. (This is true because the lift-arm is pivoting about the ball-connector (10), which is located below the level of the table, and to the right of the force measurement means.) Because the sled is already in contact with the force measurement means, it does not actually move forward but rather slides slightly at its contact with the lift-arm. Thus, as the sled is being lowered into contact with the table, and when the sled has been lowered into contact with the table, the sled is in positive contact with the force measurement means,—as required for proper initiation of the friction test.

FIG. (3) shows the apparatus at the conclusion of a first stroke of a friction test. The table has translated to the left creating a sliding motion between table and sled. The force measurement means has measured the friction force associated with that sliding motion. In preparation for the lifting of the sled (5), and the return of the table (2) to its starting position, horizontal actuator (9) has drawn the lift-arm (6) rearward (toward the right in the figure), placing the lift-arm in its down-back position.

FIG. (4) shows the apparatus after the lift-arm has been raised, lifting the sled (5) out of contact with the table (2).

Subsequent to the lifting of the sled, the table has been returned to its starting position. Due to the geometry of the lift-arm design, a clearance is created between the sled and the force measurement means as the sled is lifted. If subsequent test "passes" are to be made with the same test specimens, it is essential that each test pass is initiated from the same position as the first test pass i.e. with the sled in contact with the force measurement means. Contact can be re-established by extending the horizontal actuator (9).

FIG. (5) depicts the apparatus after the horizontal actuator (9) has been extended to move the lift-arm forward to the "up-forward" position reinstating contact between the sled (5) and the force measurement means (4). The fore-aft motion of the lift-arm (6), provided by the horizontal actuator (9), must be greater than the clearance created between sled and force measurement means during the sled-lift procedure. (In the case of the present embodiment, that motion is nominally 2 millimeters.) As the horizontal actuator moves the lift-arm forward, the lift-arm first carries the sled into contact with the force measurement means, and then causes the sled (5) to slide along the lift-arm (6) while the sled remains in contact with the force measurement means (4).

It should be apparent that FIG. (5) is the same as FIG. (1). That is, all elements of the instrument are once again in precisely the same position as for the first stroke. Thus the up/down and fore/aft mechanization of the lift-and-place means, operated according to the sequence of operations described herein, and illustrated by FIGS. (1) through (5), manipulates the lifting and placement of the sled such that every test pass is initiated from exactly the same starting condition.

The use of fore-aft movement of the lifting and placing means, coupled with the normal up-down movement is novel in the design of friction measurement apparatus. It is a practical and most effective method to achieve positive contact of the sled with the force measurement means, as the sled is being lowered into position on the table. While the above specification, and FIGS. 1–5 refer to the use of ball-connectors at the ends of link (8), and a ball-connector (10) at the connection of lift-arm (6) to horizontal actuator (9), it should be apparent that the function of the ball connector could, alternatively, be performed by a universal joint, or by a pin-and-clevis connector.

Creating a controlled static force in a kinetic friction instrument

The second of the novel means taught by the present invention concerns means for driving the table in a static/kinetic friction test. In such a test, table and sled are initially in static contact. A gradually increasing force is applied to the table (or sled) causing the friction force at the interface between table and sled to increase,—eventually to the point where sled and table begin to slide with respect to each other. The force at which they begin to slide is known as the static friction value. After the limit of static friction force has been exceeded, the table (or sled) is driven at a constant speed, and the force required to maintain sliding motion (the kinetic friction value) is measured. A problem exists, however, in that the drive means required for static and kinetic friction tests are fundamentally different. The present invention teaches means to overcome that problem.

During the static portion of the test, there is no movement of either sled or table. The drive means must apply a gradually increasing force to the table (and thus to the interface between table and sled) in a very controlled way. The force must increase over a period of several seconds to the level at which static friction limit between sled and table is reached,—and the table and sled move with respect to each other.

During the kinetic portion of the test, the drive means must produce a stable, sliding motion between table and sled, essentially independent of variations in the friction force generated between table and sled. Such drive means are termed "mechanically stiff". If the kinetic drive means is not sufficiently stiff, sliding motion between sled and table may be replaced by a rapid sequence of "stick" and "slip" movements. Because kinetic friction force cannot be determined from "stick/slip" motion, it is essential that the table drive means be sufficiently "stiff" to ensure sliding motion.

Drive means of adequate mechanical stiffness are well known within the art. They are not in themselves, however, adequate as the drive means for a static/kinetic friction instrument because a "stiff" drive is not able to control the rate of force-increase during the static phase of the friction test.

The present invention teaches a mechanization that readily provides both precise control of the force applied during the static portion of the friction test; and high stiffness during the kinetic friction test, by integrating a static-forcing means within a high-stiffness kinetic drive. The invention is schematically depicted in FIG. (6).

Shown schematically in FIG. (6) is a rigid frame (11) with fixedly attached force measurement means (12). A carrier (13) is connected to the base of the frame (11) by guide means (14) which allow the carrier to translate in linear motion with respect to the frame. A mechanically stiff, kinetic drive means (15) is fixedly attached to the frame (11) and connected to the carrier. Table (16) is shown attached to the carrier by flexible columns (17). These columns securely attach the table (16) to the carrier (13), but readily allow small-displacement, fore-aft movement of the table (16) with respect to the carrier (13). Stop (18), shown here fixedly attached to the carrier, is positioned to be in close proximity to the forward end of the table. (For the present implementation, the clearance between table and stop is nominally 0.5 millimeter.) Bellows actuator (19), with air inlet (20), is attached to carrier (13) and to the aft end of the table (16). (The bellows actuator could be any device capable of producing a well-controlled force at little or no displacement.) Sled (21) rests on the table (16), and is in contact with force measurement means (12). The friction surface to be evaluated is that area common to sled and table.

Kinetic drive means (15) is locked during the static portion of a static/kinetic friction test, and thus holds the carrier in a fixed position with respect to the frame. The static test begins as air pressure is gradually increased in bellows actuator (19) to apply a gradually increasing level of horizontal static force to the table (16). Static force applied to the table is conducted, by the friction interface between sled and table, from the table to the sled, and thence by the sled to the force measurement means (12). Thus a gradually increasing frictional force is applied to the static interface between sled (21) and table (16);—which force is measured at the force measurement means (12). When the static force applied to the interface between sled and table reaches, and then exceeds, the maximum that can be carried by the static friction between the surfaces in contact, the table (16) will slide with respect to the sled (21). The table will advance until the forward end of the table comes in contact with the stop (18). At that instant the table (16) becomes rigidly connected to the carrier. Further increases in static force applied by the actuator (19) do not create further movement, but do cause the table to be more firmly held in contact with the carrier.

With the table (16) thus rigidly connected to the carrier, the kinetic drive means can be activated to cause the carrier

(13) and "rigidly-connected" table (16) to perform the kinetic portion of the static/kinetic friction test.

The novel mechanization disclosed here combines a mechanically-stiff kinetic drive means (necessary to preclude stick/slip response in the kinetic portion of the friction test) with a small displacement, static forcing means (needed to provide a gradually increasing force profile in the static portion of the friction test)—in such a way that the static forcing means automatically becomes a rigidly connected part of the "stiff" drive means when the static forcing function is no longer needed. Thus, the stiffness characteristics of the static forcing means do not effect the stiffness of the drive system during the critical kinetic portion of the friction test. The concept taught here solves one of the fundamental challenges in the design of a static/kinetic friction measurement apparatus,—in a way that is simple, practical and economical.

Figure 6:
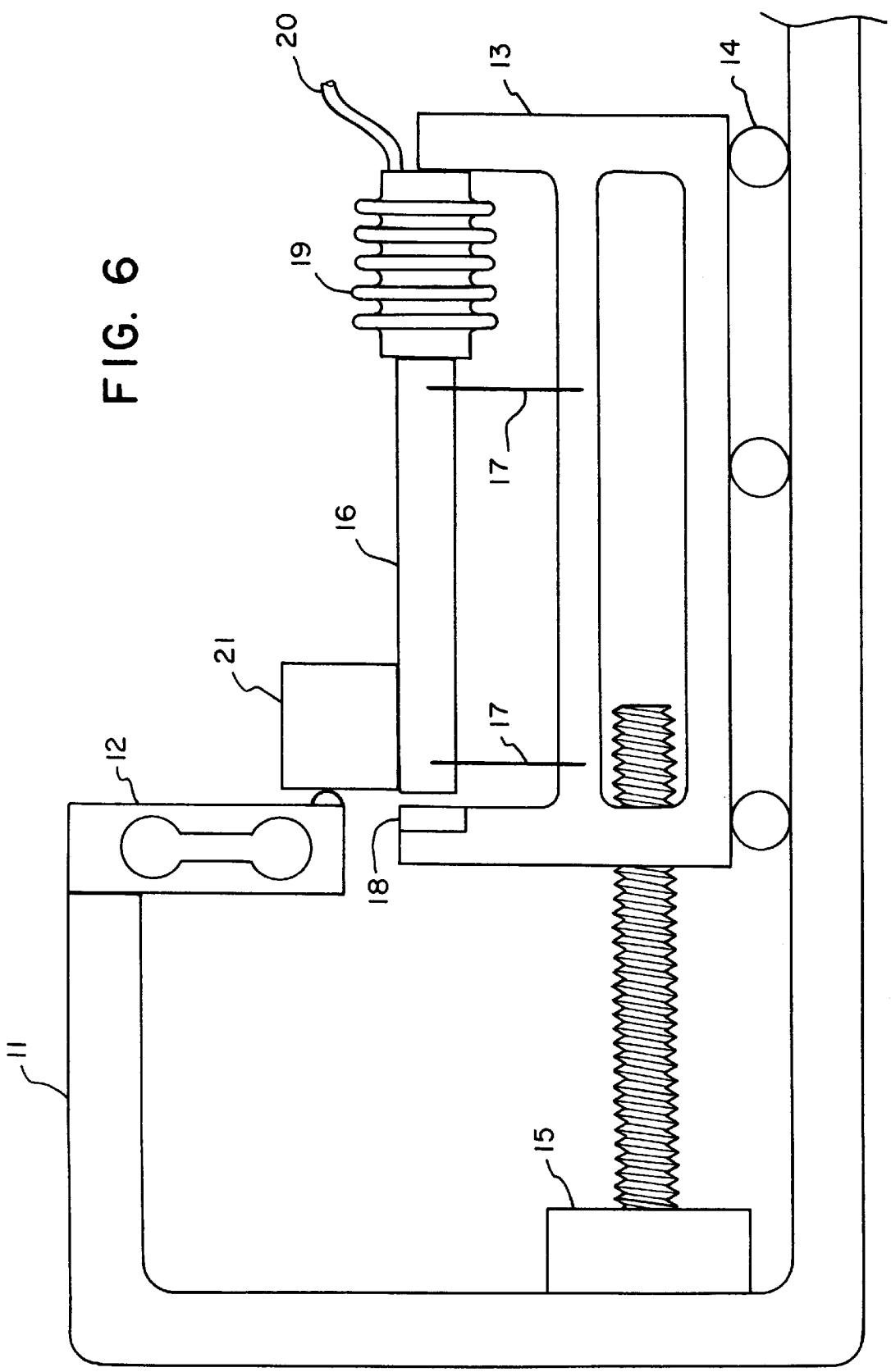

While the above specification and FIG. 6 refer to the use of a bellows (19) as the means to generate a controlled static friction force, at very small displacements, a variety of other force generating elements could be used. Elements suitable for this function include a pneumatic or hydraulic piston-in-cylinder, an electromagnet, a thermal expansion device, or a piezo-electric element.

Affixing a specimen material to the sled

Friction force, whether static or kinetic, is a measure of the material properties of the surfaces of sled and table that are in contact. Often, it is not the materials of the sled and table per se which are of interest, but rather those of specimen sheet materials which are affixed to sled and table. Because contamination, through handling, adhesive attachment means, or contact with other surfaces, can alter friction values of the test-pieces, it is useful to develop means to affix specimen materials to sled and table. Such means should allow the specimen materials to be affixed easily, and with as little potential for contamination, as possible.

Figure 7A:
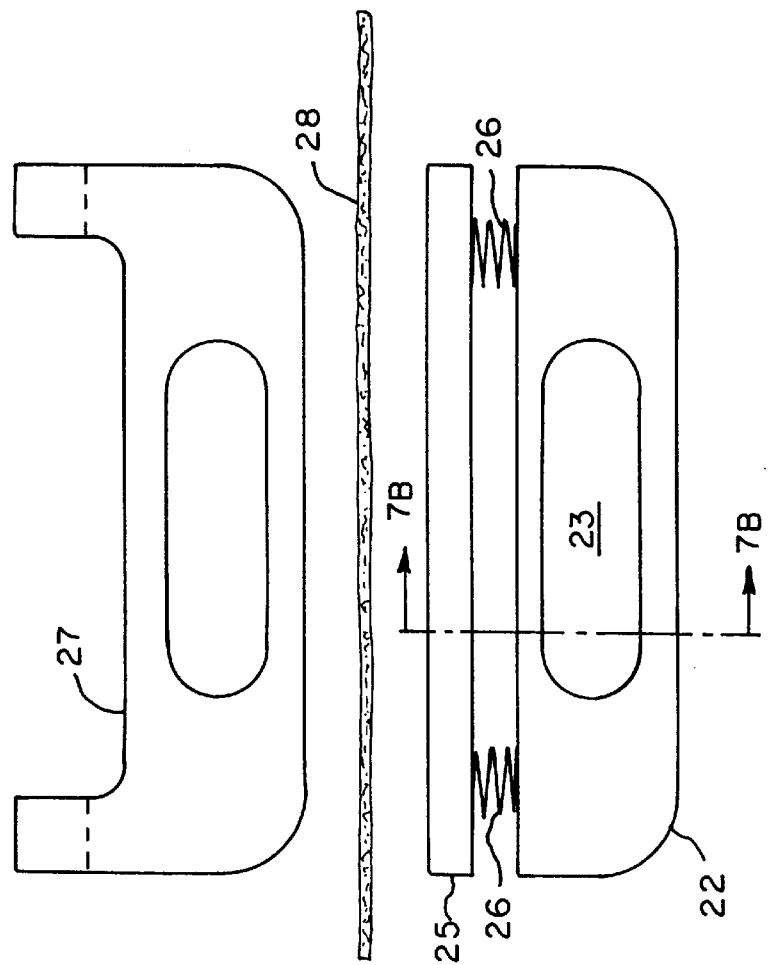
Figure 7B:
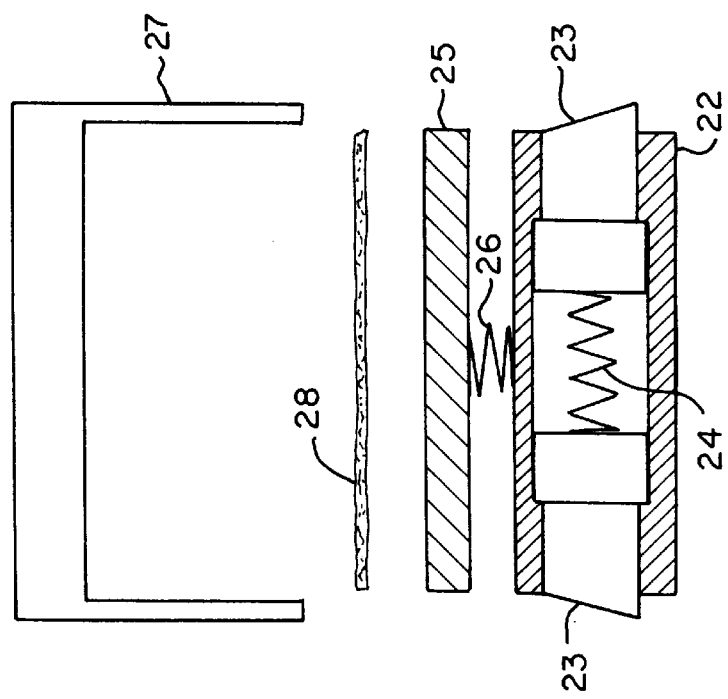
Figure 8:
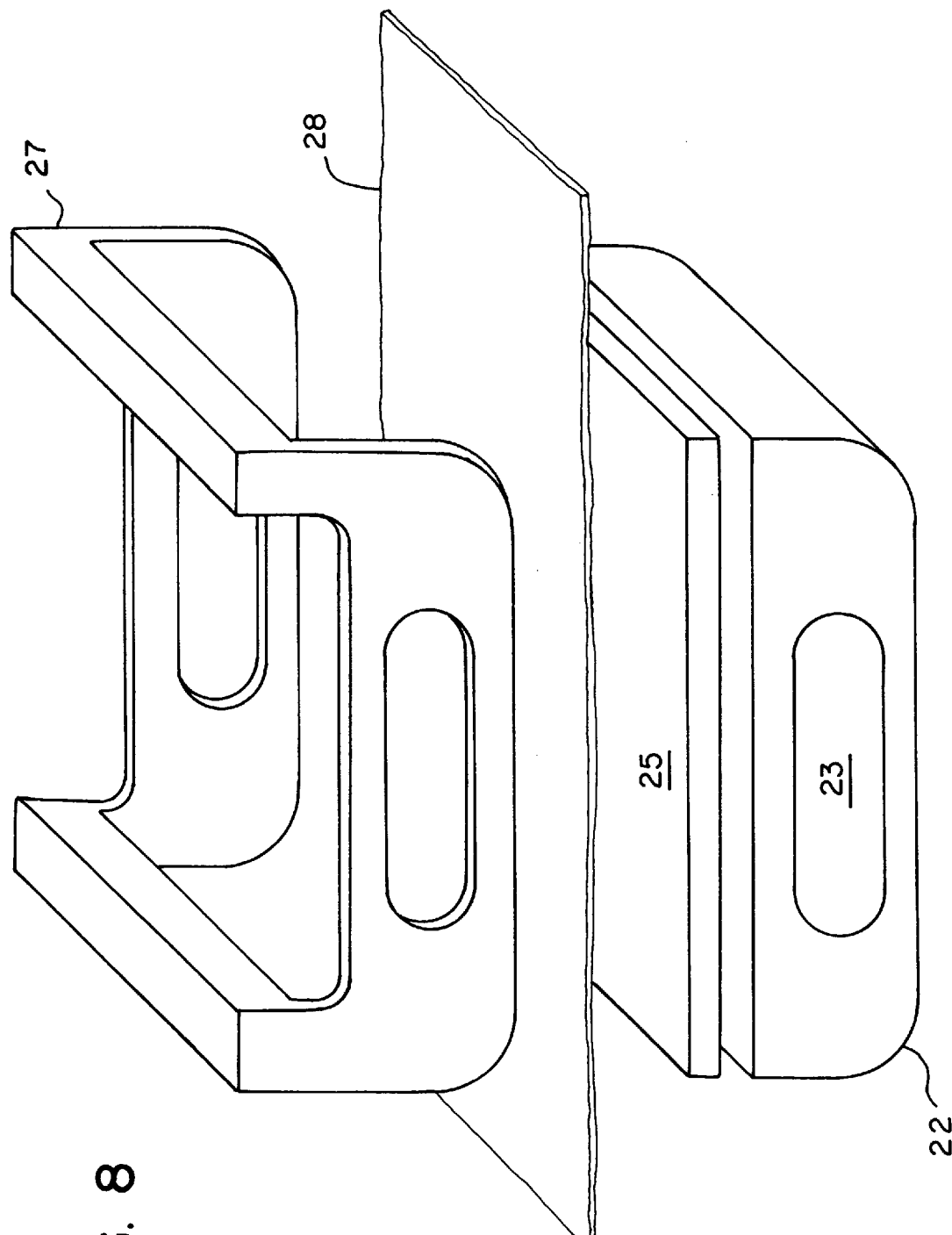

The present invention teaches such a means for affixing a test-piece of a sheet material to the sled. The invention is depicted in FIG. (7). Both an "end view" and a "side view" of the sled assembly are shown. The sled assembly comprises a block (22), two slidable latch-pieces (23) separated by a latch-spring (24); a plate (25) connected to block (22) by two compressible springs (26); and a removable clamp-piece (27). Block (22) is shown in full section view to expose the two latch-pieces (23) and the latch-spring (24). Also shown in FIG. 7 is a test-piece of specimen material (28).

Because the design of the clamp-piece (27) is not easily visualized in the orthogonal views of FIG. (7), it is also shown in isometric perspective in FIG. (8). (Component identification numbers used in FIG. (8) are consistent with those in FIG. (7)). In FIG. (8), it can be seen that the clamp piece (27) comprises two parallel clamp-bars, which cross over the test-piece (28), and two integral side-plates that can pass down over the sides of plate (25) and block (22). Oblong cutouts in the side-plates of the clamp-piece are designed to engage the latch-pieces (23) in the block (22).

Referring now to the End View of the sled assembly in FIG. (7), envision that the block (22) is supported by a horizontal surface below the block, and that the test-piece (28) is resting on the plate (25). If the clamp-piece (27) is now gradually lowered toward the plate, the side-plates of the clamp-piece will pass by the plate and the block until the parallel clamp-bars of the clamp-piece (27) rest upon the test-piece (28), holding it against the plate (25). If downward force is then applied to the parallel clamp-bars of the clamp-piece (27), the test-piece will be held between the clamp-bars of the clamp-piece and the plate (25) Increasing downward force on the clamp-piece (27) will cause the clamp-springs (26) to compress, and the plate (25) to move closer to the block (22). The clamp-piece will then slide further down over the block (22), causing the latch-pieces to be pushed back into the block (22), compressing the latch-spring (24). As the clamp-piece (27) is pushed further down, the latch-pieces will eventually engage the cutouts in the side-plates of the clamp-piece (27), and the clamp-piece will be held in place,—even as the postulated downward force on the clamp-piece is removed. In this state, the force of the compressed clamp-springs (26), pushing against the plate (25) provides the force required to secure the test-piece (28) between the plate (25) and the parallel clamp-bars of the clamp-piece (27).

To change the test-piece, the clamp-piece (27) can be easily and quickly removed by pushing the latch-pieces (23) back into the block (22) so as to disengage them from the cutouts in the side-plates of the clamp-piece (27). The clamp-piece may then be lifted straight up from the plate (25). The "old" test-piece may then be lifted off the plate, and a new test-piece set in place.

This means for affixing a test-piece to the sled is novel in that the test-piece, lies flat on a plate, and is held at its ends under compressive (clamping) force by two parallel clamp-bars that are part of a single clamp-piece. It is novel in that the sled comprises a body with latch elements, a plate mounted compressibly thereon, and a single clamp-piece comprising the two clamp bars. It is novel in that the clamping force at the two parallel clamp-bars is created by the clamp springs that compressibly mount the plate on the body, which force is transmitted by the operation of the latches-pieces which engage the clamp-piece.

The result of this novel concept and design is that the test-piece can be quickly and conveniently affixed to the sled. There is no need for tape or adhesive; no need to bend or fold the test-piece. As a consequence, the potential that the operator may accidentally contaminate the test-piece is greatly reduced; the probability that valid test results will be obtained, significantly enhanced.

What is claimed is:

1. An apparatus for measuring friction force between surfaces, said apparatus comprising; a sled, a table, a force generating means for generating a friction force therebetween, and a friction force measuring means for measuring said friction force; wherein said apparatus further comprising lift and place means for positioning said sled in contact with said table, said lift and place means comprising a lift-arm with means for providing vertical and horizontal movements to said lift arm by which said sled is placed in positive contact with said friction force measurement means while said sled is being placed in contact with said table.

2. An apparatus according to claim 1, said apparatus further comprising a frame with horizontal and vertical actuators mounted thereon, said actuators being connected to said lift-arm by connection means whereby operation of said actuators provides linear and angular displacement of said lift arm.

3. The apparatus according to claim 2, wherein said connection means comprises ball connectors.

4. The apparatus according to claim 2, wherein said connection means comprises universal joints.

5. The apparatus according to claim 2, wherein said connection means comprises pin-and-clevis joints.

6. An apparatus as recited in claim 2, wherein said vertical actuator is connected to said lift arm by vertical link and ball connectors.

7. An apparatus as recited in claim 2, wherein said horizontal actuator is connected to said lift arm by a ball-connector.

8. An apparatus according to claim 1, wherein said force generating means comprises a static force means having a small displacement gradually increasing force profile which causes the friction force at the interface between said sled and said table to increase.

9. An apparatus according to claim 8, wherein said static-force means generating comprises a bellows.

10. An apparatus according to claim 8, wherein said static force generating means comprises a pneumatic or hydraulic cylinder.

11. An apparatus according to claim 8, wherein said static force generating means comprises an electromagnet.

12. An apparatus according to claim 8, wherein said static force generating means comprises a thermal expansion device.

13. An apparatus according to claim 8, wherein said static force generating means comprises a piezo-electric element.

14. An apparatus according to claim 1, wherein said friction creating means comprises a kinetic drive means, said kinetic drive means comprising a mechanically stiff drive means free of stick/slip movement during operation.

15. An apparatus according to claim 1, wherein said force generating means comprises a static force generating means and a kinetic force generating means, wherein said static force generating means when not in operation is rigidly connected to said kinetic (drive) force generating means.

16. An apparatus according to claim 1, wherein said sled comprises a body, a plate mounted compressibly thereon and a clamp, wherein a latching means joins said body with said clamp.

17. An apparatus according to claim 16, wherein said plate is compressed on said body by operation of said latching means.

18. An apparatus according to claim 16, wherein a specimen is held in place on said plate by operation of said latching means.

19. An apparatus according to claim 16, wherein said clamp comprises parallel bars, said parallel bars clamp a specimen on said plate by means of said latching means.

* * * * *